United States Patent
Hashaikeh et al.

(10) Patent No.: US 10,850,262 B2
(45) Date of Patent: Dec. 1, 2020

(54) FIBROUS ZEOLITE CATALYST FOR HYDROCRACKING

(71) Applicant: Khalifa University of Science and Technology, Abu Dhabi (AE)

(72) Inventors: Raed Hashaikeh, Abu Dhabi (AE); Shaheen Anis, Abu Dhabi (AE); Gnana P. Singaravel, Abu Dhabi (AE)

(73) Assignee: KHALIFA UNIVERSITY OF SCIENCE AND TECHNOLOGY, Abu Dhabi (AE)

( * ) Notice: Subject to any disclaimer, the term of this patent is extended or adjusted under 35 U.S.C. 154(b) by 0 days.

(21) Appl. No.: 16/470,432

(22) PCT Filed: Dec. 19, 2017

(86) PCT No.: PCT/IB2017/058153
§ 371 (c)(1),
(2) Date: Jun. 17, 2019

(87) PCT Pub. No.: WO2018/116172
PCT Pub. Date: Jun. 28, 2018

(65) Prior Publication Data
US 2020/0009542 A1    Jan. 9, 2020

Related U.S. Application Data

(60) Provisional application No. 62/436,387, filed on Dec. 19, 2016.

(51) Int. Cl.
| | | |
|---|---|---|
| *B01J 29/06* | (2006.01) | |
| *B01J 29/16* | (2006.01) | |
| *B01J 29/14* | (2006.01) | |
| *B01J 35/06* | (2006.01) | |
| *B01J 37/00* | (2006.01) | |
| *B01J 37/03* | (2006.01) | |
| *B01J 37/04* | (2006.01) | |
| *B01J 37/08* | (2006.01) | |
| *B01J 37/34* | (2006.01) | |
| *C10G 47/04* | (2006.01) | |
| *C10G 47/18* | (2006.01) | |
| *C10G 47/20* | (2006.01) | |
| *D01D 5/00* | (2006.01) | |
| *C04B 35/626* | (2006.01) | |
| *C04B 35/622* | (2006.01) | |
| *C04B 35/634* | (2006.01) | |

(52) U.S. Cl.
CPC ........... *B01J 29/166* (2013.01); *B01J 29/146* (2013.01); *B01J 35/06* (2013.01); *B01J 37/0018* (2013.01); *B01J 37/038* (2013.01); *B01J 37/04* (2013.01); *B01J 37/088* (2013.01); *B01J 37/342* (2013.01); *B01J 37/343* (2013.01); *C04B 35/6263* (2013.01); *C04B 35/62245* (2013.01); *C04B 35/63444* (2013.01); *C10G 47/04* (2013.01); *C10G 47/18* (2013.01); *C10G 47/20* (2013.01); *D01D 5/003* (2013.01); *C04B 2235/3258* (2013.01); *C04B 2235/3279* (2013.01); *C04B 2235/3463* (2013.01); *C04B 2235/449* (2013.01); *C04B 2235/526* (2013.01); *C04B 2235/5264* (2013.01); *C04B 2235/5296* (2013.01); *C04B 2235/5445* (2013.01); *C10G 2300/70* (2013.01)

(58) Field of Classification Search
CPC ...... B01J 35/06; B01J 35/0006; B01J 35/023; B01J 37/088; B01J 37/0018; B01J 37/038; B01J 37/04; B01J 37/342; B01J 37/348; B01J 37/343; B01J 29/146; B01J 29/166; C07C 2529/08; C07C 2523/755; C07C 2523/888; C07C 2523/30; C07C 2523/70; D01D 5/003; C04B 35/62245; C04B 35/6263; C04B 35/63444; C04B 2235/526; C04B 2235/3279; C04B 2235/3463; C04B 2235/449; C04B 2235/3258; C04B 2235/5264; C04B 2235/5296; C04B 2235/5445; C10G 47/16; C10G 47/18; C10G 47/04; C10G 47/20; C10G 2300/70
USPC ......................................... 502/60, 73, 74, 79
See application file for complete search history.

(56) References Cited

U.S. PATENT DOCUMENTS

| | | | | |
|---|---|---|---|---|
| 4,362,651 | A | * | 12/1982 | Schwarzenbek ......... B01J 35/06 208/120.3 |
| 6,177,373 | B1 | * | 1/2001 | Sterte ................. B01D 67/0051 502/4 |

(Continued)

FOREIGN PATENT DOCUMENTS

| | | |
|---|---|---|
| EP | 1779929 A1 | 5/2007 |
| JP | 2000328067 A | 11/2000 |

(Continued)

OTHER PUBLICATIONS

L. Gutberlet, "Design of a Nickel-Tungsten Hydrocracking Catalyst", 1994, 227-233, Energy & Fuels, vol. 8.

(Continued)

*Primary Examiner* — Elizabeth D Wood
(74) *Attorney, Agent, or Firm* — Billion & Armitage; Lisbeth C. Robinson (57) ABSTRACT

A hydrocracking catalyst for petroleum hydrocracking is provided, the hydrocracking catalyst provided in a form of at least one fiber, and the at least one fiber comprising at least one zeolite and at least one metal oxide. Methods are also provided to form the hydrocracking catalyst in the form of at least one fiber, particularly electrospinning.

19 Claims, 10 Drawing Sheets

(56) References Cited

U.S. PATENT DOCUMENTS

| | | | | |
|---|---|---|---|---|
| 6,198,015 | B1* | 3/2001 | Marcilly | B01J 29/46 502/61 |
| 6,569,394 | B2* | 5/2003 | Fischer | B01J 29/166 423/239.2 |
| 7,507,684 | B2* | 3/2009 | Hofmann | B01D 53/9418 502/60 |
| 8,080,209 | B2* | 12/2011 | Shirono | B01D 53/9431 422/177 |
| 2007/0259770 | A1* | 11/2007 | Hofmann | B01J 29/46 502/60 |
| 2009/0214397 | A1* | 8/2009 | Shirono | B01J 21/066 422/177 |
| 2012/0178981 | A1* | 7/2012 | Corma | C10L 1/08 585/532 |
| 2015/0245547 | A1* | 8/2015 | Robinson, Jr. | B01J 20/165 424/663 |
| 2016/0121312 | A1 | 5/2016 | Zhang et al. | |
| 2016/0121315 | A1 | 5/2016 | Zhang et al. | |
| 2016/0236174 | A1* | 8/2016 | Lowry | B01J 35/0013 |
| 2019/0046967 | A1* | 2/2019 | Li | C07C 11/08 |

FOREIGN PATENT DOCUMENTS

| | | |
|---|---|---|
| WO | 2007048627 A2 | 5/2007 |
| WO | 2012161985 A1 | 11/2012 |

OTHER PUBLICATIONS

John W. Ward, "Hydrocracking Processes and Catalysts", 1993, 55-85, Fuel Processing Technology, vol. 35, Elsevier Science Publishers.

Jiancheng Di, "Fabrication of Zeolite Hollow Fibers by Coaxial Electrospinning" article, 2008, 3543-3545, Chemistry of Materials, vol. 20, No. 11.

Jiancheng Di, "Fabrication of Molecular Sieve Fibers by Electrospinning" article, 2011, 8511-8520, Journal of Materials Chemistry, vol. 21.

Shaheen Fatima Anis, "Electrospun Ni-W/Zeolite Composite Fibers for N-Heptane Hydrocracking and Hydroisomerization", Journal, 2017, 146-154, Materials Chemistry and Physics, vol. 200.

* cited by examiner

| Catalyst/ Testing temperature | Conversion of n-heptane (wt. %) | Selectivity for n-hexane (wt. %) | Selectivity for iso-hexane (wt. %) |
|---|---|---|---|
| Ball milled zeolite-WO$_3$-NiO fiber [350°C] | 98.81 | 19.87 | 39.35 |
| Ball milled zeolite-WO$_3$-NiO fiber [400°C] | 96.81 | 50.71 | 18.90 |

FIBROUS ZEOLITE CATALYST FOR HYDROCRACKING

CROSS-REFERENCE TO RELATED APPLICATIONS

This application claims the benefit of U.S. provisional application No. 62/436,387 filed Dec. 19, 2016, which is hereby incorporated by reference in its entirety.

FIELD

The present disclosure relates generally to catalysts, and more specifically to fibrous zeolite catalysts for hydrocracking.

BACKGROUND

With the rising global economy and population, and the consequent accelerated demand for energy and productivity, there has been a serious need for more efficient catalysts to fulfill these requirements. In today's world, one of the major areas where the catalysis is of key importance is the crude oil refining process, where maximizing the product yield and quality while minimizing the process cost and energy consumption are the key challenges. This requirement calls for an optimum chemical composition, and systematic physical hierarchy of different phases inside a catalyst for enhanced chemical activity and hence higher throughput.

Whereas the crude oil refining comprises of a series of 'cracking' steps, the major and the crucial cracking step is 'hydrocracking' which involves the conversion of high boiling point hydrocarbons to more valuable products, such as gasoline and diesel in addition to other intermediate distillates. Because of high-temperature and high-pressure requirements, conventional hydrocracking has been replaced by the 'mild hydrocracking' process, where the reaction is carried out at a lower temperature and much lower pressure. However, to provide enough energy for the reaction, we need an efficient catalyst which does not only sustain the reaction, but also gives the desired product quantity and quality.

In hydrocracking, the catalyst is bi-functional performing the 1) 'cracking' action which involves the chain scission of high molecular weight hydrocarbons and the 2) 'hydrogenation' action which involves the saturation of cracking products or other unsaturates present in the feed-stock. Typically, the cracking action is achieved by the alumina-silica phase whereas the hydrogenation action is achieved by the metal/metal oxide component. Thus the hydrocracking catalyst has at least two components performing the cracking and hydrogenation actions, respectively. Existing hydrocracking catalysts are applied in the form of pallets ranging from several hundred microns to a couple of millimeters in size. The alumina-silica phase generally acts as a matrix enclosing the metal/metal oxide phase. Due to the larger physical size of the catalyst, lower surface area and hence lesser availability of active sites, the resultant product yield is still below the desired and theoretical values.

SUMMARY

A hydrocracking catalyst for petroleum hydrocracking is provided, the hydrocracking catalyst provided in a form of at least one fiber, and the at least one fiber comprising at least one zeolite and at least one metal oxide. Methods are also provided to form the hydrocracking catalyst in the form of at least one fiber, particularly electrospinning. A distinguishing feature of the catalyst is the ease of accessibility of the reactants to the active sites, which is achieved by the open structure the (nano) fiber form provides without the presence of binding materials (to bind the metal oxide and zeolite together). Hence, the catalyst may be understood to have no binder material, and thus binder free.

In at least one embodiment, the at least one zeolite may be a Y-zeolite. The Y-zeolite may be a CBV series zeolite having a hydrogen cation form. The Y-zeolite may have a $SiO_2/Al_2O_3$ mole ratio of at least 3 to 1.

In at least one embodiment, the at least one metal oxide may be one of nickel oxide, tungsten trioxide, cobalt oxide and molybdenum trioxide. More particularly, the at least one metal oxide may be nickel oxide or tungsten trioxide.

In at least one embodiment, the at least one metal oxide further comprises at least a first metal oxide and a second metal oxide. More particularly, the first metal oxide may be nickel oxide, and the second metal oxide may be tungsten trioxide.

In at least one embodiment, 81-87% by weight of the at least one fiber may comprise the at least one zeolite, and 1-19% by weight of the at least one fiber may comprise the at least one metal oxide. More particularly, 85-87% by weight of the fiber may comprise the at least one zeolite, and 2-10% by weight of the fiber may comprise the at least one metal oxide.

In at least one embodiment, the at least one fiber may have a length in a range of 0.1-500 microns, and the at least one fiber may have a diameter in a range of 50-800 nanometers. More particularly, the at least one fiber may have a length in a range of 50-500 microns, and the at least one fiber may have a diameter in a range of 500-800 nanometers. Even more particularly, the at least one fiber may have a length in a range of 450-500 microns, and the at least one fiber may have a diameter in a range of 520-630 nanometers.

In at least one embodiment, the at least one fiber may have a length-to-diameter aspect ratio in a range of 50:1 to 1,000:1. More particularly, at least one fiber may have a length-to-diameter aspect ratio in a range of 800:1 to 1,000:1, and more particularly 900:1 to 1,000:1.

In at least one embodiment, the at least one fiber may have a surface area in a range of 240-300 square meters/gram.

In at least one embodiment, the at least one fiber may comprise a plurality of fibers. More particularly, the plurality of fibers may form a fiber mat, in which the fibers may be randomly orientated.

In at least one embodiment, a method of making a hydrocracking catalyst for petroleum hydrocracking is provided, comprising creating a mixture comprising at least one zeolite in a form of zeolite nano-particles, nickel acetate, ammonium metatungstate, ethanol and water; stirring the mixture; sonicating the mixture; obtaining a stable suspension of the mixture; adding polyvinylpyrrolidone to the mixture; and electrospinning the mixture.

In at least one embodiment, the method of making a hydrocracking catalyst for petroleum hydrocracking may further comprise forming at least one fiber from electrospinning of the mixture, the at least one fiber comprising the at least one zeolite.

In at least one embodiment, the method of making a hydrocracking catalyst for petroleum hydrocracking may further comprise the at least one fiber further comprising the nickel acetate, the ammonium metatungstate and the polyvinylpyrrolidone from the mixture; calcinating the at least one fiber; removing the polyvinylpyrrolidone from the at least one fiber while calcinating the at least one fiber;

forming nickel oxide from the nickel acetate while calcinating the at least one fiber such that the at least one fiber further comprises the nickel oxide; and forming tungsten trioxide from the ammonium metatungstate while calcinating the at least one fiber such that the at least one fiber further comprises the tungsten trioxide.

In at least one embodiment, the method of making a hydrocracking catalyst for petroleum hydrocracking may comprise adding the polyvinylpyrrolidone to the mixture after obtaining the stable suspension of the mixture, and electrospinning the mixture after adding the polyvinylpyrrolidone to the mixture.

In at least one embodiment, the method of making a hydrocracking catalyst for petroleum hydrocracking may comprise stirring the mixture and sonicating the mixture simultaneously.

In at least one embodiment, the method of making a hydrocracking catalyst for petroleum hydrocracking may comprise providing a weight ratio of the zeolite nano-particles to the nickel acetate ranges from 1:0.1 to 1:0.15; a weight ratio of the zeolite nano-particles to the ammonium metatungstate ranges from 1:1.5 to 1:1.8; a weight ratio of the zeolite nano-particles to the polyvinylpyrrolidone ranges from 1:0.7 to 1:1; a weight ratio of the zeolite nano-particles to the ethanol ranges from 1:5 to 1:5.2; and a weight ratio of the zeolite nano-particles to the deionized water ratio ranges from 1:4 to 1:4.2.

In at least one embodiment, the method of making a hydrocracking catalyst for petroleum hydrocracking may comprise the zeolite nano-particles having a size in a range of 50-350 nanometers. More particularly, the zeolite nano-particles may have a size in a range of 150-200 nanometers.

In at least one embodiment, the method of making a hydrocracking catalyst for petroleum hydrocracking may comprise forming the zeolite nano-particles using a ball mill. More particularly, the zeolite nano-particles may be formed using a ball mill from zeolite particles having a size in a range of 600-700 nanometers.

In at least one embodiment, a method of making a hydrocracking catalyst for petroleum hydrocracking is provided, comprising creating a mixture comprising at least one zeolite, at least one metal oxide precursor, at least one polymer, ethanol and water; obtaining a stable suspension of the mixture; and electrospinning the mixture.

In at least one embodiment, the method of making a hydrocracking catalyst for petroleum hydrocracking may comprise forming at least one fiber from electrospinning of the mixture, the at least one fiber comprising the at least one zeolite, the at least one metal oxide precursor and the at least one polymer; calcinating the at least one fiber; removing the at least one polymer from the at least one fiber while calcinating the at least one fiber; and forming at least one metal oxide from the at least one metal oxide precursor while calcinating the at least one fiber such that the at least one fiber further comprises the at least one metal oxide.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

DETAILED DESCRIPTION

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

A hydrocracking catalyst is disclosed herein, suitable for petroleum (hydrocarbon) hydrocracking, which catalyst may be particularly formed in the geometry of a strand, particularly as a nano-fiber/wire. The catalyst may comprise at least one zeolite and/or at least one metal oxide. The catalyst may by in the form of a plurality of nano-fibers/wires, such as a nano-fiber/wire mat.

The catalyst may be prepared by electrospinning (ES) a stable suspension which at least includes nano-particles of zeolite. Such a catalyst may exhibit desirable activity and selectivity in, for example, hydrocracking processes, such as heptane hydrocracking.

In accordance with embodiments disclosed herein, a one-dimensional nano-structured catalyst for hydrocracking is disclosed that provides high surface area and hence more effective catalytic action.

Zeolites are crystalline hydrated networks of alumina (also known as aluminum oxide ($Al_2O_3$)) and silica (also known as silicon dioxide ($SiO_2$)) possessing ordered porosity at the molecular level. Such networking and porosity makes them highly efficient catalysts in chemical reactions. Several classes of zeolite exist based on the composition, pore size and the crystalline structure, and can be employed as catalysts in different petroleum refining processes. Based on the type of zeolite used as the catalyst, the output differs significantly in terms of yield, conversion efficiency, and selectivity. Effective catalysis may be based, at least in part, on surface area. With increased surface area there may be greater availability of active sites. Therefore, there has been growing interest in synthesizing nano-scale zeolites to achieve higher catalytic activity and hence higher efficiency and product yield.

ZSM (Zeolite Socony Mobil) zeolites may be synthesized in the form of nano-particles in the size range of 35 to 200 nm, and FAU (Faujasite) and LTA (Linde Type A) may be synthesized in the size range of 40 to 80 nm Various parameters affecting the nano-zeolite size, crystallinity, and yield may include chemical choices, their proportion, addition sequence, and appropriate synthesis duration.

The zeolite nano-particles may be obtained in the form of homogeneous suspensions which may be applied across the porous alumina matrix, so that they may be applied in real-time applications. Such encapsulation of nano-zeolites may also provide benefits to their structural integrity and stability of performance in various applications such as a heterogeneous catalysis.

Zeolite nano-particles with a size range of 10 to 20 nm may be uniformly dispersed across the alumina matrix. As far as their performance is concerned, the catalytic efficiency is inversely proportional to zeolite particle size. For instance, in the case of FAU type zeolite, the percentage conversion of the feed oil may increase with decreasing size of zeolite nano-crystal. Moreover, the product selectivity may be dependent upon the size of zeolite nano-crystal. Similarly, the conversion efficiency and product yield may be higher in the case of various nano-zeolites as compared to their macroscopic counterparts.

For a particular zeolite employed as a catalyst in hydrocracking, the term 'activity' may refer to the overall efficiency of the catalyst in converting the particular feedstock into the respective products and the term 'selectivity' may refer to the relative inclination of the catalyst towards a specific reaction (e.g., the relative yield of a particular product). Based on the feedstock type, plant operating conditions, and the desired yield of specific products, a variety of zeolites having meso-porous structure may be synthesized as catalysts in hydrocracking. Each catalyst may be unique in terms of zeolite phase crystalline structure, its relative composition of alumina and silica, and the amount of a particular metal/metal oxide present for hydrogenation. A particular combination of these parameters leads to specific activity and selectivity. For example, the zeolitic phase of hydrocracking catalyst consists of a high silica to alumina molar ratio (generally a silica to alumina molar ratio of 3 or higher) are referred to as 'Y zeolites'. Zeolites with a low silica to alumina molar ratio (generally a silica to alumina molar ratio of less than 3) are referred to as 'X zeolites.' The low alumina molar ratio may lead to a deficiency of aluminum atoms in the zeolite framework. The deficiency may be overcome by $H^+$ ions, which may lead to the formation of more acidic sites which lead to increased catalytic activity. An example of such zeolite is FAU type, which is a commonly used catalyst in hydrocracking. It has a 12 membered ring of Al and Si atoms arranged in a 3D channel network. This results in a molecular sieve formation having a relatively large pore size of 0.74 nm Since the feedstock of hydrocracking is composed of large and heavy hydrocarbons, the large pore size of FAU zeolite allows these large hydrocarbon molecules to easily access the active sites. On the other hand, the specific structure of FAU zeolite provides specific selectivity for the output products. Typical products of hydrocracking are liquid petroleum gas (LPG), high octane gasoline, naphtha products, diesel, and jet fuel. Several other types of zeolites such as LTL (Linde Type L) and MFI (Mordenite Framework Inverted) with their characteristic framework and pore size may also be used for obtaining specific selectivity.

As far as the metal oxide component of the hydrocracking catalyst is concerned, which may be integrated directly with zeolite, or in the amorphous matrix holding the catalyst, may function to keep the acidic sites active. This may be achieved by hydrogenating the intermediate unsaturated hydrocarbons formed during the cracking reaction. At the same time, it may also help in the formation of some intermediate products. Thus, the metal oxide phase greatly affects the activity as well as selectivity of the hydrocracking catalyst. Various types of metals such as Nickel (Ni), Platinum (Pt), Palladium (Pd), and Molybdenum (Mo) and various types of metal oxides such as molybdenum trioxide ($MoO_3$), ferric oxide ($Fe_2O_3$), tin dioxide ($SnO_2$), and titanium dioxide ($TiO_2$) may be used in various hydrocracking applications for a desired activity and selectivity. The role of a particular metal may change significantly during hydrocracking in the presence of different metal oxide catalyst supports.

Electron transport may be based, at least in part, on choice of chemical specie. The physical architecture of a catalyst may include hierarchical interconnection, porosity, and the increased surface area for greater availability of active sites. Due to the very high surface area, the 'nano-scale' or the 'nano-structured' catalysts have turned out to be very promising in this regard. However, the approach of disintegrating the micro-particles to nano-particles may not be applicable when it comes to enhanced activity of a catalyst due to the agglomeration of nano-particles, which may cause a large proportion of active sites to become inaccessible.

Figure 1A:
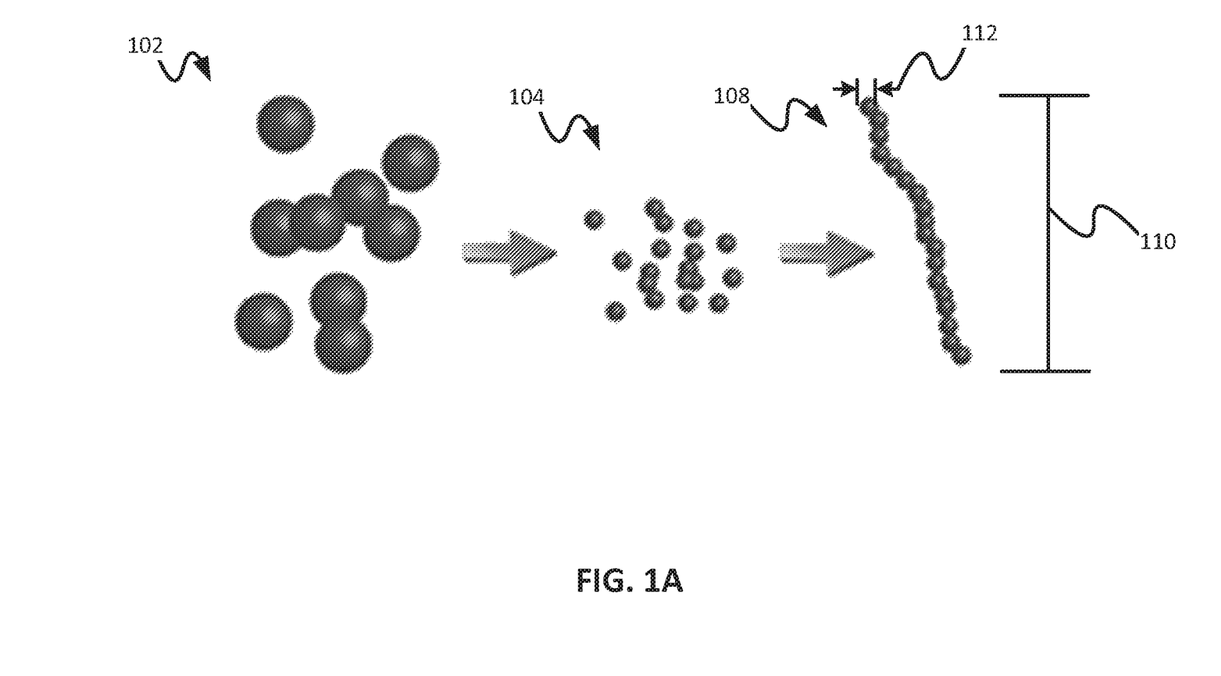
FIG. 1A schematically shows micro-particles broken down to nano-particles which are arranged linearly to form a strand, which may be more particularly referred to as a nano-fiber or nano-wire (according to size), consistent with embodiments of the present disclosure.

Referring now to the figures, FIG. 1A shows a schematic example of micro-particles 102 being converted into nano-particles 104, such that the nano-particles 104 can define/form a strand, particularly a nano-fiber/wire 108. The nano-fiber/wire 108 may represent an approach for taking advantage of the nano-scale. The nano-fiber/wire 108 provides a linear one-dimensional (elongated) shape that may have a length 110 which ranges from 0.1 microns (μm) to 500 microns (μm), more particularly ranges from 50 microns (μm) to 500 microns (μm), and even more particularly ranges from 450 microns (μm) to 500 microns (μm); while the diameter of the nano-fiber/wire 108, which corresponds to the width 112, may range from 50 nanometers (nm) to 800 nanometers (nm), more particularly range from 500 nanometers (nm) to 800 nanometers (nm), and even more particularly range from 520 nanometers (nm) to 630 nanometers (nm). With respect to aspect ratio, which may be understood as length-to-diameter ratio, such may be in a range of 50:1 to 1,000:1, and more particularly in a range of 800:1 to 1,000:1, and even more particularly in a range of 900:1 to 1,000:1. With respect to specific surface area, such may be in a range of 240-300 square meters/gram ($m^2$/gram)

Figure 1B:
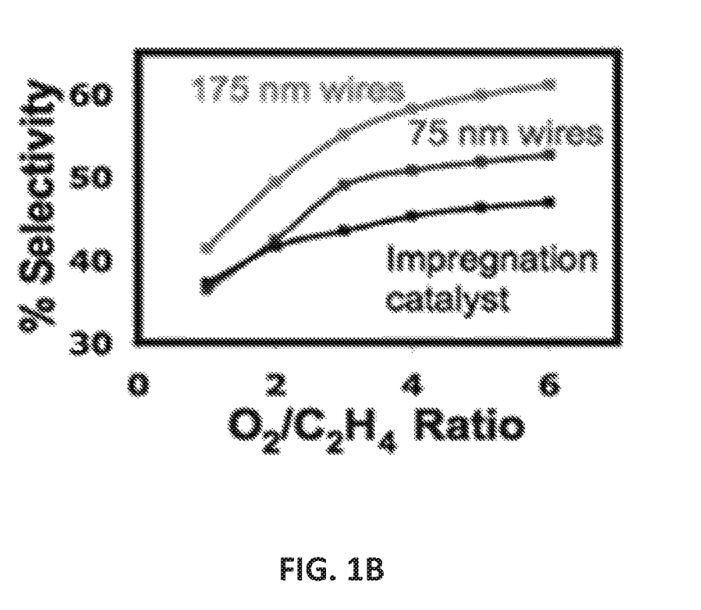
FIG. 1B is a plot of catalytic selectivity of silver (Ag) nano-fiber/wire vs nano-particles, consistent with embodiments of the present disclosure.
Figure 1C:
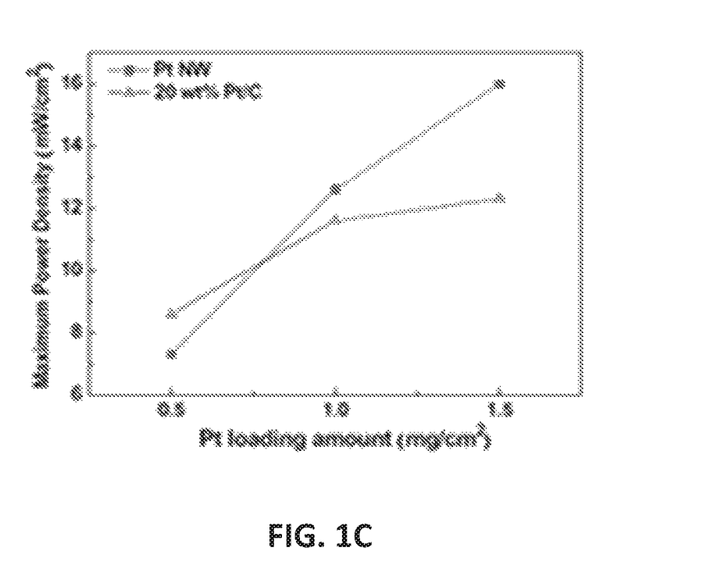
FIG. 1C is a plot of maximum power density for a given current in case of platinum (Pt) nano-fiber/wire and platinum (Pt) nano-particles, consistent with embodiments of the present disclosure.

The nano-fiber/wire 108 as disclosed may eliminate the agglomeration issue and also may impart sufficient weight and volume to the catalyst, which aids in the catalyst recovery. Moreover, different phases inside a catalyst can be systematically and homogenously confined at the nano-scale. As shown in FIGS. 1B and 1C, the catalytic performance of nano-fiber/wire 108 may be superior to their nano-particle counterpart. This behavior may be explained in terms of better electron transport in nano-fiber/wire 108 due to less collision across interfaces. The impregnation catalyst of FIG. 1B is based on particles. FIG. 1B also illustrates a diameter dependence in the nano-fiber/wire 108.

Electrospinning, which is an economic and industrially scalable technique, is a powerful and versatile method for fabricating nano-fiber/wire 108 with varying diameter, length, and/or morphology (e.g., porous, core-shell etc.). The uniqueness and versatility of electrospinning lies in its physical nature. For example, a precursor solution may have to be prepared having the desired nano-fiber/wire material and then carry out its electrospinning under a suitable flow rate and voltage to come up with a nano-fiber/wire shape. Therefore, the electrospinning process may be used for fabricating ultra-high surface area one-dimensional nano-structured hierarchically porous materials with various compositions that can be applied in a desired catalytic application. Such nano-fiber/wire 108 with rough morphology and very high porosity are potential catalysts in various petroleum refining processes such as 'hydrocracking.'

As mentioned earlier, the zeolite nano-particles may be integrated inside a porous matrix in real-time applications because, if used standalone, not only would their recovery be nearly impossible because of their extremely low weight and size, but they will also be prone to excessive attrition and clustering leading to a dramatic decrease in their catalytic activity with time. It should be noted that, although the porous alumina matrix encapsulating the zeolite nano-particles may eliminate these problems, the catalytic efficiency of the nano-particles may also be decreased at the same time since a large part of the nano-particles surface is not exposed to take part in the reaction. This may be overcome by shaping the nano-particles into a nano-fiber/wire form. While the diameter/width 112 of the nano-fiber/wire 108 may impart high surface area and, consequently, increased availability of active sites, the length 110 may provide sufficient weight and volume to solve the recovery problem. Moreover, the nano-fiber wire 108 may be less prone to clustering and attrition as compared to nano-particles. Also, because of their length, effective electron transport, low resistance to fluid flow, and ease of fabricating and incorporating in membrane forms, heterogeneous catalytic applications may benefit from the nano-fiber/wire 108.

One approach to producing zeolite nano-fiber/wire 108 may involve depositing zeolite clusters on various types of inorganic fibers. This approach may be based, at least in part, on modifying the fiber surface and then exposing the fiber to the appropriate chemicals and processing conditions which leads to systematic growth of zeolite crystals around the fiber. The result may be the formation of core-shell structure (zeolite shell surrounding the inorganic fiber core). In some cases, the inorganic fiber core can be later removed to end up with hollow zeolite nano-fiber/wire. This approach can be used with different types of zeolites coated on glass, carbon, and silica fibers. Following very much same approach, the nano-scale growth of Y-zeolites may be possible. For example, zeolite nano-crystals in the size range of 10-500 nm (nanometers) may be grown over titania (also known as titanium dioxide $TiO_2$)) nano-fibers having an average diameter of about 100 nm. These zeolite nano-crystals may display superior catalytic performance. Moreover, zeolite nano-crystals falling within the size range of 50-100 nm (nanometers) may possess the maximum catalytic conversion efficiency.

Synthesis of the zeolite nano-fiber/wire 108 may be achieved using carbon nano-tubes as a template. BETA zeolite nano-fiber/wire may be synthesized within the carbon nano-tubes, which may then be selectively removed via calcination. This may result in the formation of BETA zeolite nano-fiber/wire. As compared to commercially available BETA zeolite, BETA zeolite nano-fiber/wire may exhibit significantly higher conversion efficiency and selectivity during the catalytic test. Other techniques such as hydrothermal, without using any template, may be used for synthesis of SUZ-4 zeolite nano-wire/fiber.

As discussed herein, electrospinning is a technique for fabricating different types of nano-fiber/wire 108. Selection of precursor chemicals and their composition can lead to nano-fiber/wire 108 of virtually any materials with desired composition. Several types of nano-fiber/wire 108 may be synthesized via electrospinning and used in different catalytic applications. One approach to fabricating nano-fiber/wire 108 using electrospinning may use DAM-1 (Dallas Amorphous Material-1) and SBA-15 (Santa Barbara Amorphous-15) zeolites. The approach may involve preparing a viscous gel consisting of silica source and a structure directing agent. The gel may be electrospun under appropriate conditions to obtain the nano-fiber/wire 108. The solution viscosity may be increased such that the nano-fiber/wire morphology changes from 'highly beaded' to 'smooth and bead free.'

Following the same approach, electrospun nano-fiber/wire of MCM-41 (Mobil Composition of Matter-41) and SBA-15 zeolites may also be fabricated, using an equal proportion of polymer in the precursor solution to impart sufficient viscosity for smooth and continuous electrospinning. Once the nano-fiber/wire 108 is formed, the polymeric component may be selectively removed via heat treatment leaving behind pure zeolite nano-fiber/wire 108, with a diameter/width in the nanometer range. The morphology of zeolites may change from more 'particle like' to more 'fiber like' as the electrospinning voltage and the distance increases. Electrospun membranes of zeolitic imidazolate framework (ZIF) zeolite have may also be fabricated which may display superior gas permeability and hydrogen selectivity. Using co-axial electrospinning, hollow zeolite nano-fiber/wire may be fabricated for imparting greater surface area to the catalyst.

In order to achieve much higher activity and selectivity in hydrocracking, there has been growing interest in employing both the zeolites as well as the metal oxide, or metal/metal oxide, in the nano-structured form. Several combinations of nano-zeolites and nano-metal/metal oxides may be used as catalysts in hydrocracking of various feedstock types such as light gas oil, heavy gas oil and vacuum gas oil. Increased conversion efficiency may be observed for the nano-structured catalysts.

Therefore, electrospinning technique may be used for shaping the zeolites and metal/metal oxides in the form of nano-fiber/wire 108 such that the electrospun catalysts may be used in hydrocracking. One such catalyst may include a composite nano-fiber/wire 108 including metal oxide (e.g., nickel oxide (NiO), copper oxide (CuO)) and zeolite. This may be achieved by electrospinning the metal oxide (metallic salt) precursor including zeolite nano-particles. Another such catalyst may include forming monolithic metal oxide (or metal/metal oxide) nano-fiber/wire and monolithic zeolite nano-fiber/wire separately, however, by simultaneous electrospinning. This may result in the formation of fiber mat formed of metal oxide (or metal/metal oxide) nano-fiber/wire and zeolite nano-fiber/wire.

Example Fabrication of Electrospun Metal Oxide and Zeolite Catalysts into Nano-Fiber/Wire A metal oxide and zeolite catalyst may be formed from a mixture including one or more of dried zeolite nano-particles, nickel acetate ($C_4H_6NiO_4$) particles (powder), ammonium metatungstate ($H_{26}N_6O_{40}W_{12}$) particles (powder), ethanol, water, and/or polyvinylpyrrolidone (PVP). In some instances, the mixture may include dried zeolite nano-particles, nickel acetate salt, ammonium metatungstate salt, ethanol, deionized water, and PVP. The dried zeolite nano-particles may have a size (largest dimesion) in a range of 50 nanometers (nm) to 350 nanometers (nm), and more particularly a size in a range of 150 nanometers (nm) to 200 nanometers (nm).

The proportions of the ingredients may be calculated with respect to zeolite for zeolite-metallic salts, zeolite-polymer and zeolite-ethanol/water solvents. For example, in an exemplary embodiment, the zeolite nano-particles to the nickel acetate ratio ranges from 1:0.1 to 1:0.15 by weight respectively. The zeolite nano-particles to ammonium metatungstate ratio ranges from 1:1.5 to 1:1.8 by weight respectively. The zeolite nano-particles to polyvinylpyrrolidone ratio ranges from 1:0.7 to 1:1 by weight respectively. For the solvents, the zeolite nano-particles to ethanol ratio ranges from 1:5 to 1:5.2 by weight respectively, and the while zeolite nano-particles to deionized water ratio ranges from 1:4 to 1:4.2 by weight respectively. In some instances, the quantity of nickel acetate and ammonium metatungstate is such that 2.6% and 10% of nickel oxide (NiO) and tungsten trioxide ($WO_3$) (also known as tungsten (VI) oxide) are obtained after calcination, respectively.

The mixture may be ultrasonicated and stirred substantially continuously, preferably stirring the mixture continuously while simultaneously ultrasonicating the mixture. The dried zeolite nano-particles, nickel acetate and ammonium metatungstate suspension in ethanol/water mixture was ultrasonicated for 5-7 hours using a Branson 1510 model (the machine has fixed parameters and the only thing which can be varied is the time of sonication) to provide a stable suspension. The term 'stable' here refers to the fact that the zeolite nano-particles were evenly dispersed in the overall suspension. The nano-particles (because of their nano size) may easily settle down at the bottom of the beaker. Therefore, long sonication times are required after which the nano-particles do not settle down at the bottom of the beaker and this was confirmed through visually viewing the beaker. Therefore, stable suspension means the range between 0 to 1% of the zeolite nano-particles detected at the bottom of the beaker for a period of 30 minutes after sonication.

Figure 2A:
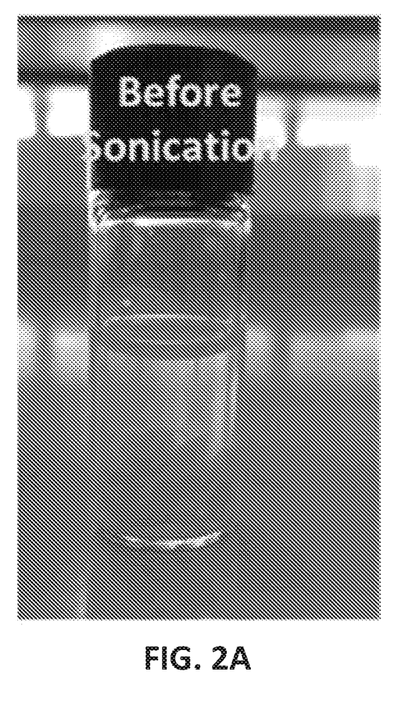
FIG. 2A shows the visual appearance of a nano-fiber/wire mat before sonification, consistent with embodiments of the present disclosure.
Figure 2B:
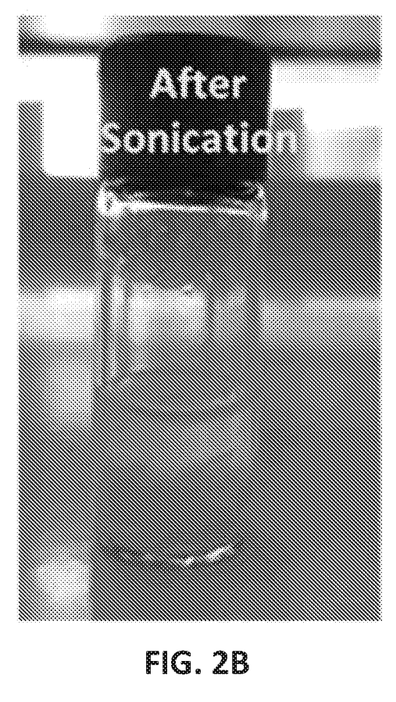
FIG. 2B shows the visual appearance of a nano-fiber/wire mat after sonification, consistent with embodiments of the present disclosure.
Figure 2C:
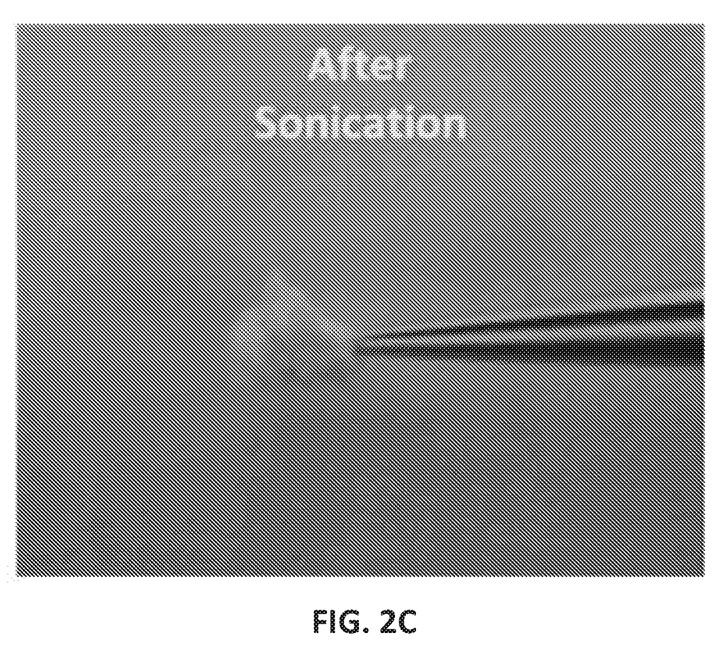
FIG. 2C shows the visual appearance of a nano-fiber/wire mat after sonification, consistent with embodiments of the present disclosure.
Figure 3A:
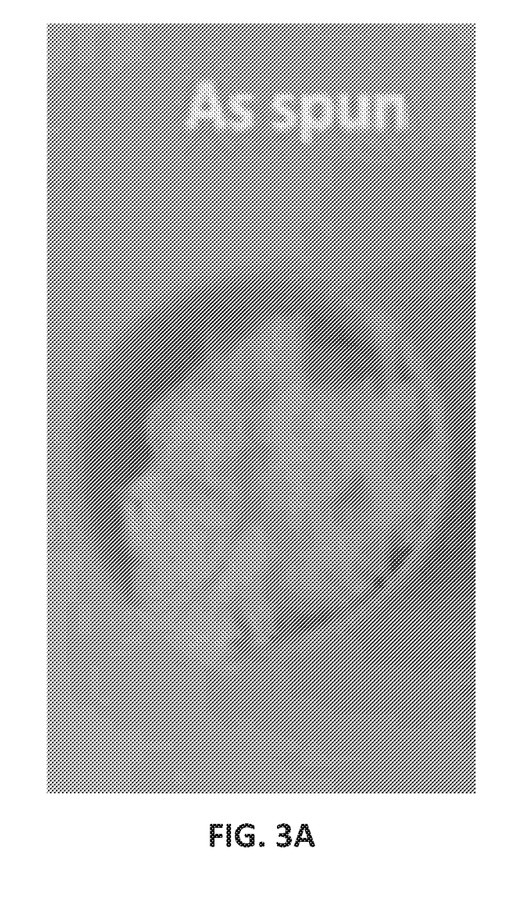
FIG. 3A shows the visual appearance of a nano-fiber/wire mat before calcination, consistent with embodiments of the present disclosure.
Figure 3B:
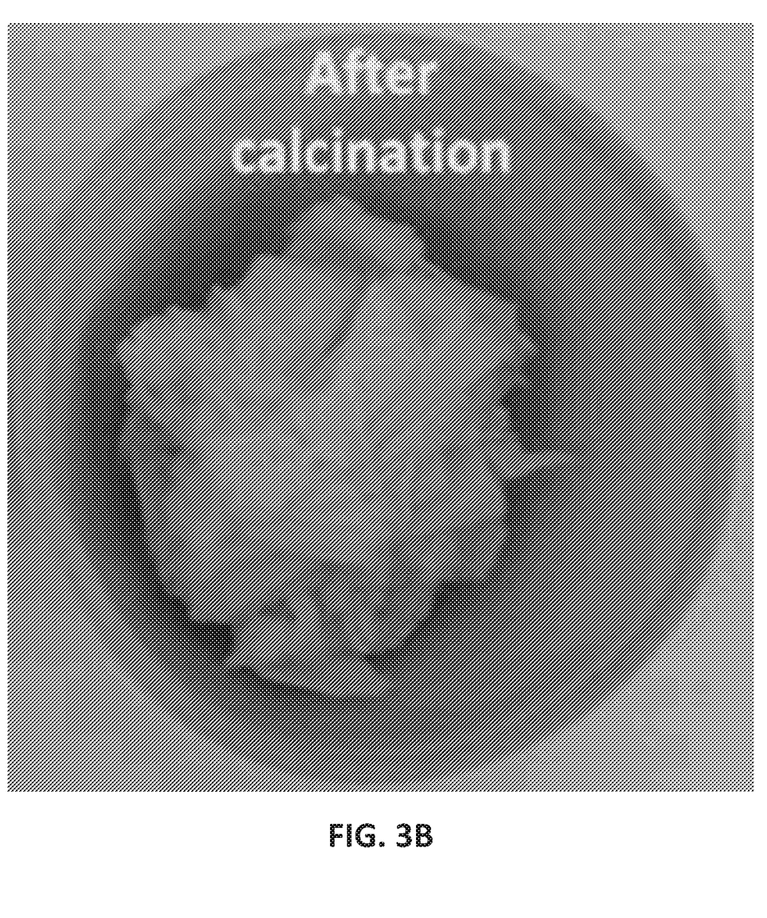
FIG. 3B shows the visual appearance of a nano-fiber/wire mat after calcination, consistent with embodiments of the present disclosure.
Figure 4A:
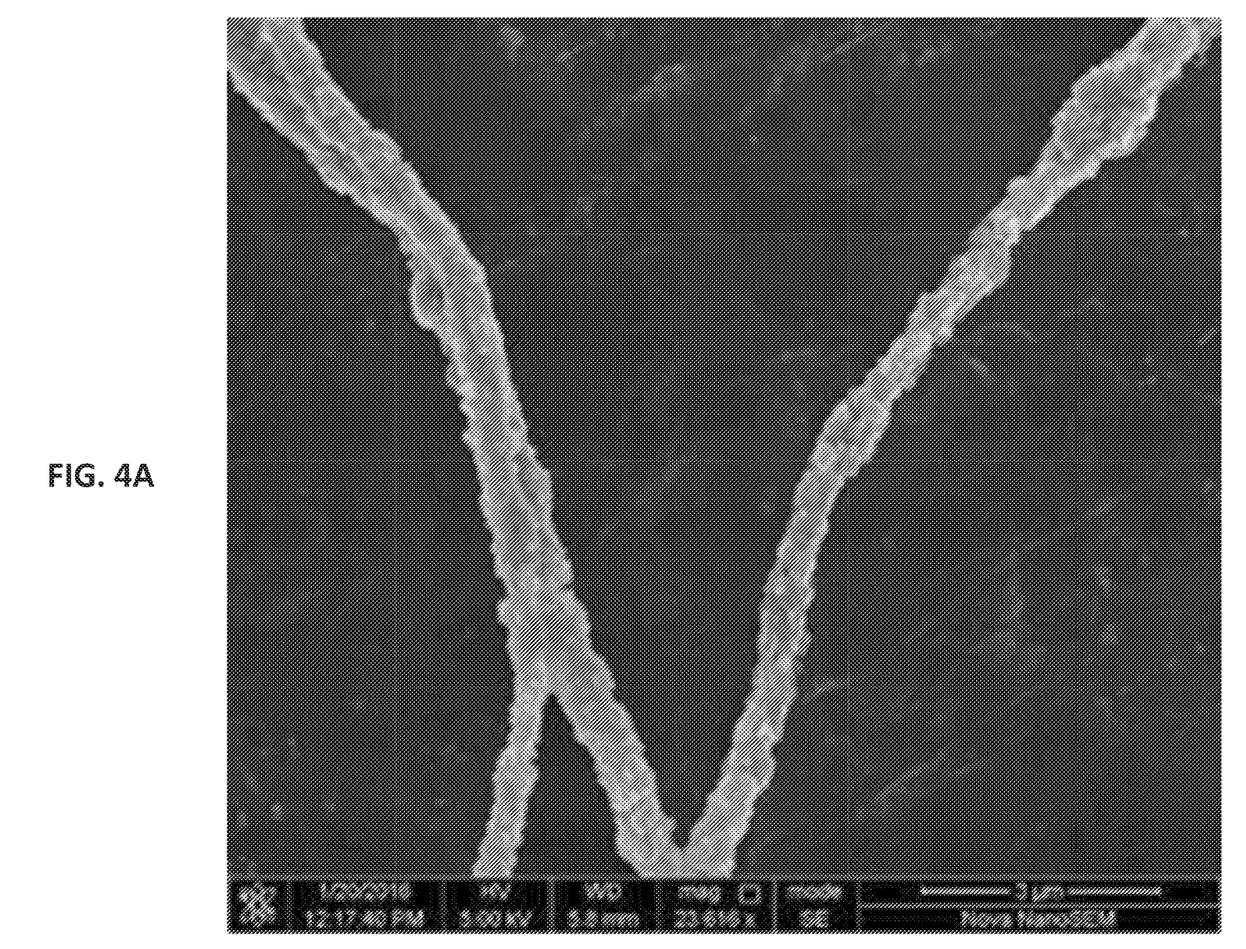
FIG. 4A shows the morphology of a nano-fiber/wire mat under a scanning electron microscope, consistent with embodiments of the present disclosure.
Figure 4B:
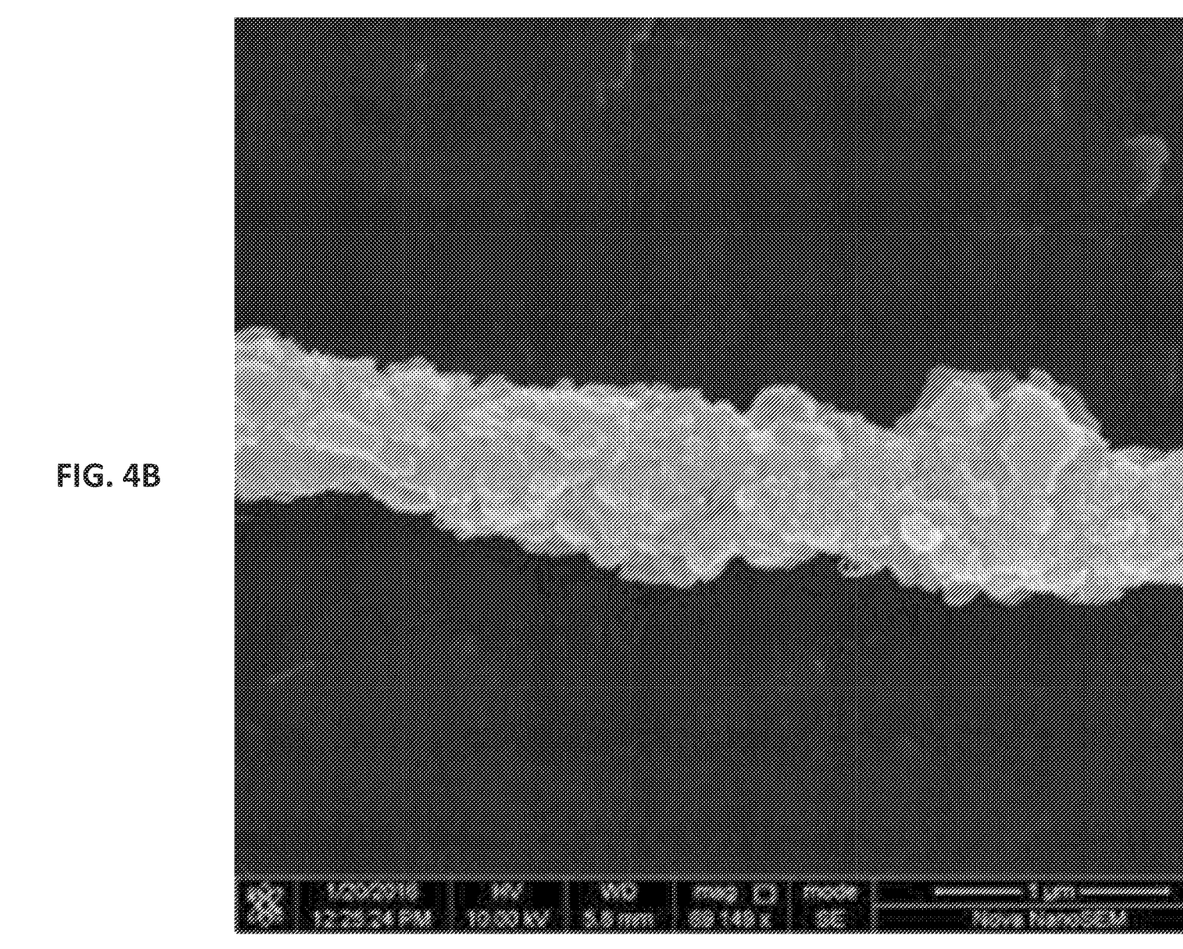
FIG. 4B shows the morphology of the a nano-fiber/wire mat under a scanning electron microscope at a different magnification than that of FIG. 4A, consistent with embodiments of the present disclosure.

Once a stable suspension is obtained, the mixture may be subjected to electrospinning (ES). After ultrasonication, polyvinylpyrrolidone was added to this homogeneous suspension and the overall electrospinning solution was then magnetically stirred for 6 hours to dissolve the polymer in the solution completely. The electrospinning may be carried out at a voltage of 28 kV, a spinning distance of 15 cm, a suspension flow rate of 0.5 mL/h, and a 21 gauge needle sufficient to form electrospun zeolite fibers. After electrospinning, the as spun fibers may be calcined at 550° C. for 2 hours using a ramp rate of 1° C./min. The calcined sample may be characterized using a scanning electron microscope (SEM) to determine a morphology and ultrasonication in water to estimate the mechanical strength. FIG. 2A shows the visual appearance of the zeolite nano-fiber/wire mat before sonification and FIGS. 2B-2C show the visual appearance of the zeolite nano-fiber/wire mat after sonification. FIGS. 3A-3B show the visual appearance of the zeolite nano-fiber/wire mat before and after calcination, respectively. FIGS. 4A-4B show the morphology of the zeolite nano-fiber/wire mat under a scanning electron microscope at different magnification levels. As shown, a diameter/width of the zeolite nano-fiber/wire may be in a range of 607.2 nanometers (nm) to 686.0 nanometers (nm). Also as shown, the plurality of nano-fibers/wires of the nano-fiber/wire mat are randomly orientated.

Depending on the ratios of the ingredients used to form the nano-fibers/wires may comprise a range of 81 percent to 87 percent by weight of the zeolite and a range of 1 percent to 19 percent by weight metal oxide, and more particularly a range of 85 percent to 87 percent by weight of the zeolite and a range of 2 percent to 10 percent by weight metal oxide.

The zeolite nano-particles may be obtained from, for example, a ball-milled sample prepared from commercially available H-Y zeolite (i.e. the nominal cation form of the zeolite is hydrogen). The Y-zeolite may have a degree of crystallinity of at least 35 percent.

The H-Y zeolite may particularly be of the CBV series, and more particularly be CBV-720. CBV-720 is was utilized due to a high silica to alumina molar ratio ($SiO_2/Al_2O_3$) of 30 to 1 (however, it should be understood that a ratio of 3 to 1 or higher, such as at least 30 to 1, is within the realm of the present disclosure). CBV-720 also has a unit cell size of 24.28 Å (angstroms), a surface area of 780 square meters/gram ($m^2/g$) and a sodium oxide ($Na_2O$) percent weight of 0.03.

Prior to being ball milled, the H-Y zeolite may have a particle size in a range of 600-700 nanometers (nm). The ball-milling may be carried out at 1,000 rotations-per-minute (rpm) for 30 minutes using 0.5 millimeter (mm) ball size. After ball-milling, the bigger particles may be separated from the nano-particles using centrifugation. The centrifugation may be carried out at, for example, 5000 rpm for five minutes. The top part centrifuged sample containing the nano-particles may be separated from the bottom part centrifuged sample (containing flakes/slabs/unground micro-size particles) using decantation. After separation of the nano-particles from the unground micro-sized particles, any remaining water may be evaporated by drying the nano-particles in an oven to obtain dried nano-particles.

Figure 5:
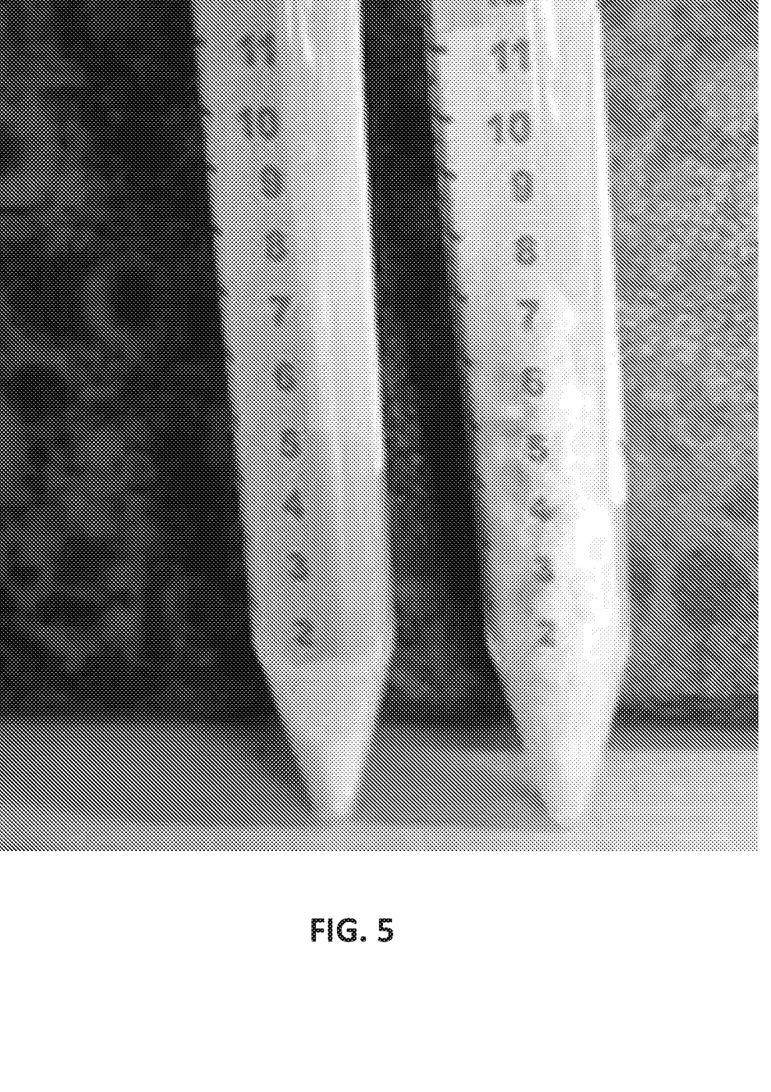
FIG. 5 shows a volume difference between comparable sample sizes of nano-particles v. nano-fibers.

By way of example, referring to FIG. 5, there is shown to vials of similar mass of 200 grams of Y-zeolite/tungsten trioxide/nickel oxide (Y-WO3-NiO) composition, with the vial on the left showing ball milled Y-zeolite/tungsten trioxide/nickel oxide (Y-WO3-NiO) particles, and the vial on the right showing the ball milled Y-zeolite/tungsten trioxide/nickel oxide (Y-WO3-NiO) fibers, formed using the electrospinning process of the present disclosure. As shown, the fibers occupy more volume, which facilitates easier catalyst recovery after the catalytic reaction.

Figure 6:
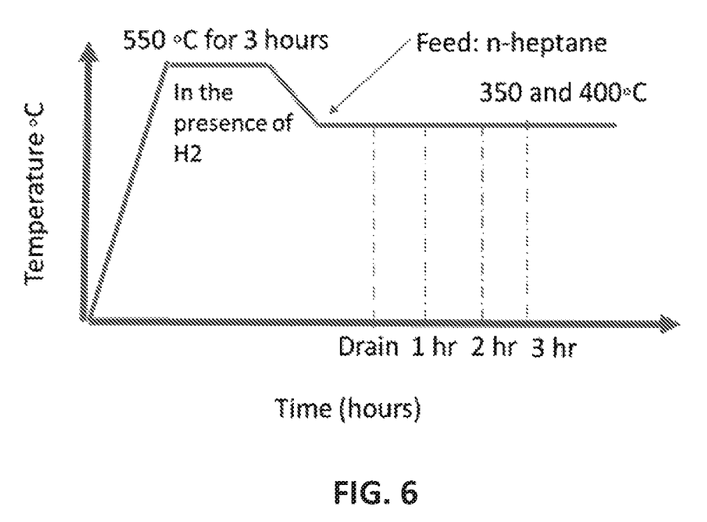
FIG. 6 is a plot of a temperature program that may be used in (n–)heptane hydrocracking, consistent with embodiments of the present disclosure.

Example Catalytic Test of Electrospun Metal Oxide and Zeolite Catalysts of Nano-Fiber/Wire The catalytic activity of the prepared catalyst was assessed using heptane hydrocracking as a model of reaction, as shown in FIG. 6. For the heptane hydrocracking model reaction, the catalyst weight was 500 mg. As shown, the hydrogen reduction conditions were 550° C. for 3 hours while the testing temperatures were 350° C. and 400° C., weight hourly space velocity (WHSV) of 4 hours$^{-1}$, feed flow rate of 0.05 ml/min., hydrogen flow of 3 NL/hr. and a hydrogen pressure of 5 bars.

Figure 7:
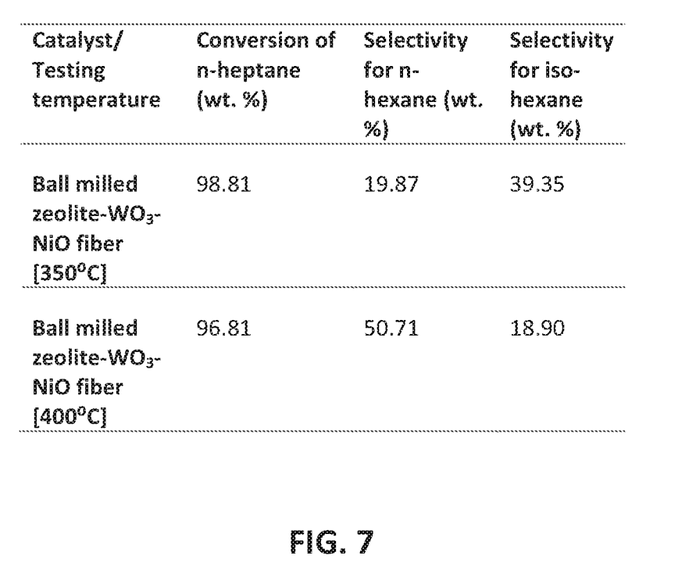
FIG. 7 is shows major product selectivity for n-heptane hydrocracking reaction at the end of total TOS.
Figure 8:
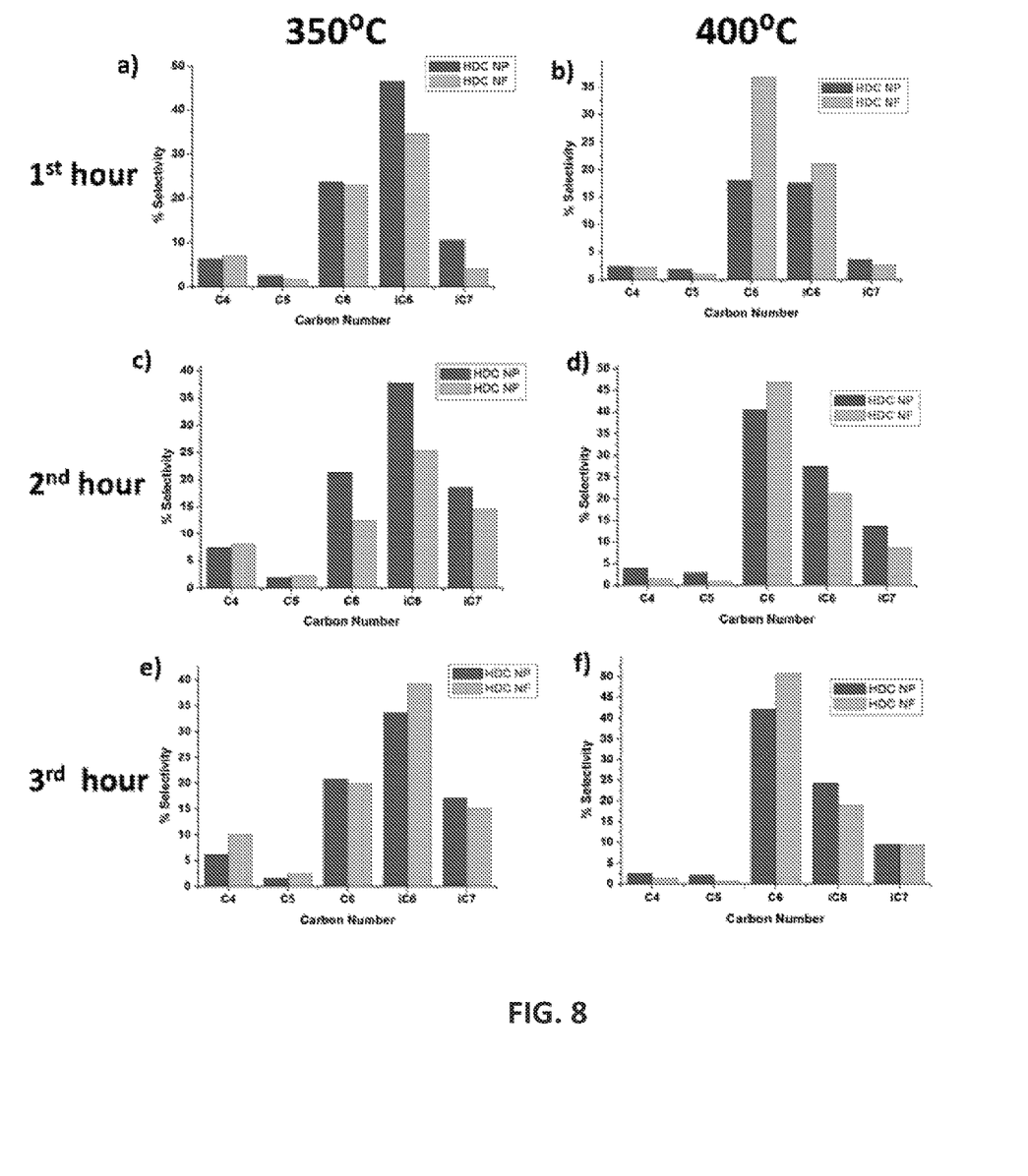
FIG. 8 shows product selectivity for ball milled Y-zeolite/tungsten trioxide/nickel oxide (Y-WO3-NiO) particles (HDC NP) verses ball milled Y-zeolite/tungsten trioxide/nickel oxide (Y-WO3-NiO) fibers (HDC NF), at 350° C. and 400° C. for each of the first, second and third hours of the reaction.
Figure 9:
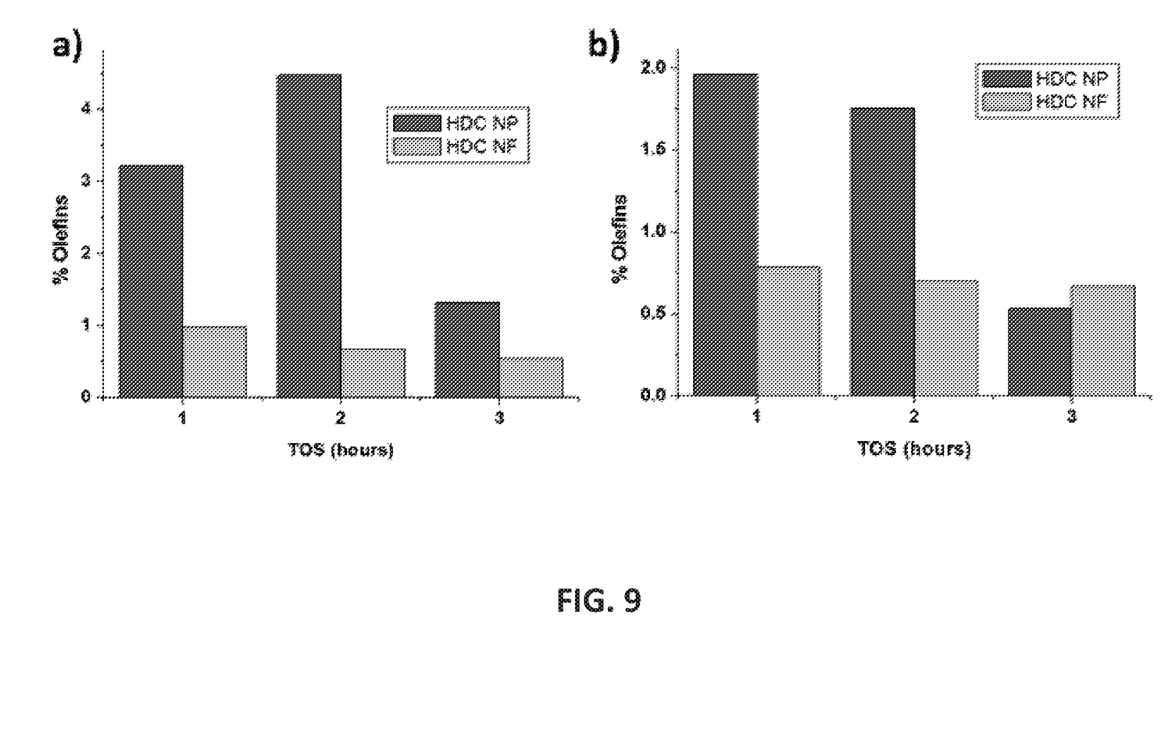
FIG. 9 shows olefin formation for ball milled Y-zeolite/tungsten trioxide/nickel oxide (Y-WO3-NiO) particles (HDC NP) verses ball milled Y-zeolite/tungsten trioxide/nickel oxide (Y-WO3-NiO) fibers (HDC NF), at 350° C. and 400° C. for each of the first, second and third hours of the reaction.

Referring to FIGS. 7-9, there is shown certain results for the heptane hydrocracking model reaction of FIG. 6. Referring to FIG. 7, while the weight percent of conversion of n-heptane remains within about 2% at temperatures of 350° C. and 400° C., the selectively for n-hexane more than doubled at 400° C. versus 350° C., while the selectivity for iso-hexane doubled at 350° C. versus 400° C.

Referring to FIG. 8, there is shown product selectivity for ball milled Y-zeolite/tungsten trioxide/nickel oxide (Y-WO3-NiO) particles verses ball milled Y-zeolite/tungsten trioxide/nickel oxide (Y-WO3-NiO) fibers, at 350° C. and 400° C. for each of the first, second and third hours of the reaction. As shown, the label HDC NF represents the ball milled Y-zeolite/tungsten trioxide/nickel oxide (Y-WO3-NiO) fibers, while the label HDC NF represents the ball milled Y-zeolite/tungsten trioxide/nickel oxide (Y-WO3-NiO) particles.

Referring to FIG. 9, there is shown olefin formation for ball milled Y-zeolite/tungsten trioxide/nickel oxide (Y-WO3-NiO) particles verses ball milled Y-zeolite/tungsten trioxide/nickel oxide (Y-WO3-NiO) fibers, at 350° C. and 400° C. for each of the first, second and third hours of the reaction. Again, the label HDC NF represents the ball milled Y-zeolite/tungsten trioxide/nickel oxide (Y-WO3-NiO) fibers, while the label HDC NF represents the ball milled Y-zeolite/tungsten trioxide/nickel oxide (Y-WO3-NiO) particles.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

While the disclosure has been described particularly making use of Y-zeolite, any zeolite may be suitable as long as it may be used for hydrocracking. Other exemplary zeolites contemplated by the present disclosure, which may be used for hydrocracking, may include ZSM-5 ("Zeolite Socony Mobil-5"), an aluminosilicate zeolite belonging to the pentasil family of zeolites. Other metal oxides which may be used with the disclosure include cobalt oxide ($Co_3O_4$) and molybdenum trioxide ($MoO_3$). Other polymers may include poly vinyl alcohol and polyethylene glycol.

LISTING OF REFERENCE CHARACTERS 102 microparticles
104 nanoparticles
108 nanowire
110 nanowire length
112 nanowire width

What is claimed is:

1. A hydrocracking catalyst for petroleum hydrocracking, comprising:
   at least one fiber comprising zeolite nanoparticles and at least one metal oxide, wherein the fiber has a diameter in the range of 50-800 nm, 81-87% by weight of the at least one fiber is the zeolite nanoparticles and 2-10% by weight of the at least one fiber is the at least one metal oxide.

2. The catalyst of claim 1, wherein:
   the zeolite nanoparticles are Y-zeolite.

3. The catalyst of claim 2, wherein:
   the Y-zeolite has a $SiO_2/Al_2O_3$ mole ratio of at least 30 to 1.

4. The catalyst of claim 1, wherein:
   the at least one metal oxide is one of nickel oxide and tungsten trioxide.

5. The catalyst of claim 1, wherein:
   the at least one metal oxide further comprises at least a first metal oxide and second metal oxide.

6. The catalyst of claim 5, wherein:
   the first metal oxide is nickel oxide; and
   the second metal oxide is tungsten trioxide.

7. The catalyst of claim 1, wherein:
   85-87% by weight of the at least one fiber is the zeolite nanoparticles.

8. A hydrocracking catalyst for petroleum hydrocracking, comprising:
   the hydrocracking catalyst provided in a form of at least one fiber; and
   the at least one fiber comprising at least one zeolite and at least one metal oxide, wherein:
   the at least one fiber has a length in a range of 0.1-500 microns; and
   the at least one fiber has a diameter in a range of 50-800 nanometers.

9. The catalyst of claim 1, wherein:
   the at least one fiber has a length-to-diameter aspect ratio in a range of 50:1 to 1,000:1.

10. The catalyst of claim 1, wherein:
    the hydrocracking catalyst is binder free.

11. The catalyst of claim 1, wherein:
    the at least one fiber comprises a plurality of fibers.

12. The catalyst of claim 11, wherein:
    the plurality of fibers form a fiber mat.

13. The catalyst of claim 1, wherein the zeolite nanoparticles have a size in a range of 50-350 nm, and a percent crystallinity greater than 35%.

14. A method of making a hydrocracking catalyst for petroleum hydrocracking, comprising:
    creating a mixture comprising zeolite nanoparticles, at east one metal oxide precursor, at least one polymer, ethanol and water;
    obtaining a stable suspension of the mixture;
    electrospinning the mixture to form a fiber having a diameter in the range of 50-800 nm; and
    calcinating the at least one fiber to remove the at least one polymer from the at least one fiber and to form at least one metal oxide from the at least one metal oxide precursor;
    whereby 81-87% by weight of the at least one fiber is the zeolite nanoparticles and 2-10% by weight of the at least one fiber is the at least one metal oxide.

15. The method of claim 14, further comprising ball-milling zeolite microparticles to produce the zeolite nanoparticles.

16. The method of claim 14, wherein the at least one metal oxide precursor comprises nickel acetate and ammonium metatungstate.

17. The method of claim 16, wherein the at least one polymer is polyvinylpyrrolidone.

18. The method of claim 17, wherein:
   a weight ratio of the zeolite nanoparticles to the nickel acetate ranges from 1:0.1 to 1:0.15;
   a weight ratio of the zeolite nanoparticles to the ammonium eta tungstate ranges from 1:1.5 to 1:1.8;
   a weight ratio of the zeolite nanoparticles to the polyvinylpyrrolidone ranges from 1:0.7 to 1:1;
   a weight ratio of the zeolite nanoparticles to the ethanol ranges from 1:5 to 1:5.2; and
   a weight ratio of the zeolite nanoparticles to the water ratio range from 1:4 to 1:4.2.

19. The method of claim 14, wherein the zeolite nanoparticles have a size in a range of 50-350 nm, and a percent crystallinity greater than 35%.

* * * * *